United States Patent [19]

Lucas et al.

[11] Patent Number: 4,931,548

[45] Date of Patent: Jun. 5, 1990

[54] HETERODIMER FORM OF TRANSFORMING GROWTH FACTOR-BETA

[75] Inventors: Roger C. Lucas, Blaine; James A. Weatherbee, St. Anthony; Monica L.-S. Tsang, St. Anthony, all of Minn.

[73] Assignee: Techne Corporation, Minneapolis, Minn.

[21] Appl. No.: 8,808

[22] Filed: Jan. 30, 1987

[51] Int. Cl.$^5$ .................... C07K 13/00; A61K 37/24
[52] U.S. Cl. .................... 530/399; 530/300; 530/380; 530/356; 530/827; 530/829; 530/840; 530/350; 514/885; 514/886; 514/921
[58] Field of Search ............... 530/299, 350, 300, 380, 530/827, 829; 514/2, 21, 12, 8

[56] References Cited

U.S. PATENT DOCUMENTS

| | | | |
|---|---|---|---|
| 4,434,094 | 2/1984 | Seyedin et al. | 260/112 |
| 4,563,350 | 1/1986 | Nathan et al. | 424/95 |
| 4,627,982 | 12/1986 | Seyedin et al. | 424/95 |
| 4,774,322 | 9/1988 | Seyedin et al. | 530/353 |
| 4,806,523 | 2/1989 | Bentz et al. | 514/2 |

FOREIGN PATENT DOCUMENTS

| | | |
|---|---|---|
| 0132021 | 1/1985 | European Pat. Off. ............... 424/85 |
| 0169016 | 1/1986 | European Pat. Off. . |
| 9200341 | 12/1986 | European Pat. Off. . |
| 0213776 | 5/1987 | European Pat. Off. . |
| WO/8401106 | 3/1984 | PCT Int'l Appl. . |
| 8401106 | 3/1984 | World Int. Prop. O. ............... 514/2 |

OTHER PUBLICATIONS

Assdian et al., JBC 258, 1983, pp. 7155–7160.
Wahl et al., PNAS, 84, 1987, pp. 5788–5792.
Seyedin et al., JBC 261, 1986, pp. 5693–5695.
Roberts et al., Biochemistry 22(25), 1983, pp. 5692–5698.
Marquarilt et al., Science 223, 1984. pp. 1079–1081.
Childs et al., PNAS 79, 1982, 5312–5316.
Sporn et al., Science 219, 1983, pp. 1329–1320.
Derynik et al., JBC 261, 1986, pp. 4377–4379.
"Heterodimeric Transforming Growth Factor Beta-Biological Properties and Interaction with Tree Types of Cell Surface Receptors", Cheifetz, et al., Journal of Biological Chemistry, vol. 263, Aug. 5, 1988, pp. 10783–10789.
Trends in Biochem. Sci., vol. 10, pp. 239–240. (1985), J. Massague, "The Transforming Growth Factors".
Science, vol. 233, pp. 532–534 (1986), M. B. Sporn, et al; "Transforming Growth Factor–beta: Biological Function and Chemical Structure".
J. of Biol. Chem., vol. 261, pp. 5693–5695 (May 5, 1986), S. Seyedin; "Cartilage–Inducing Factor–A: Apparent Identity to Transforming Growth Factor–Beta".
Proc. Natl. Acad. Sci. USA, vol. 82, pp. 2267–2271 (April 1985), S. Seyedin, et al.; "Purification and Characterization of Two Cartilage–Inducing Factors from Bovine Demineralized Bone".
Collagen Corporation Annual Report, 1987.
Collagen Corporation, 10 pages.
J. of Biol. Chem., vol. 261, pp. 9972–9978 (Jul. 25, 1986); S. Chelfetz et al.; "Cellular Distribution of Type I and Type II Receptors for Transforming Growth Factor–Beta".
Cell, vol. 48, pp. 409–414 (Feb. 13, 1987); S. Cheifetz, et al.; "The Transforming Growth Factor–Beta System, a Complex Pattern of Cross–Reactive Ligands and Receptors".
Biochemistry, vol. 22 (1983), "Purification and Properties of Type $\beta$ Transforming Growth Factor from Bovine Kidney" (Roberts), pp. 5692–5698.
J. Biol. Chem., vol. 256 (Jun. 1983), "Transforming Growth Factor–$\beta$–In Human Platelets", (Assoian), pp. 7155–7160.

Primary Examiner—Garnette D. Draper
Attorney, Agent, or Firm—Gregory P. Kaihoi; James R. Haller; Mary P. Bauman

[57] ABSTRACT

A polypeptide transforming growth factor found in procine platelets, having activity in the TGF-$\beta$ assay and a molecular weight of about 25 kDa. The factor is a heterodimer, one chain of which has an N-terminal sequence very different from human platelet TGF-$\beta$, and the other chain of which has an N-terminal sequence identical to that of human platelet TGF-$\beta$. The factor is purified using gel filtration and reverse phase HPLC.

2 Claims, 4 Drawing Sheets

FIG. 3A
Form 1
FIG. 3B
Form 2
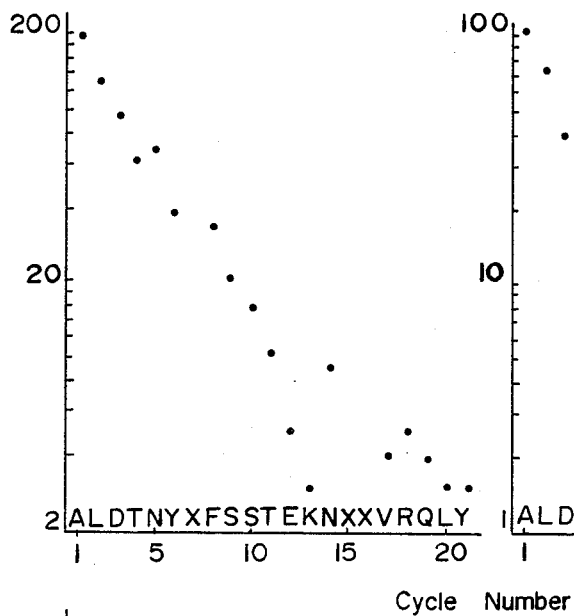
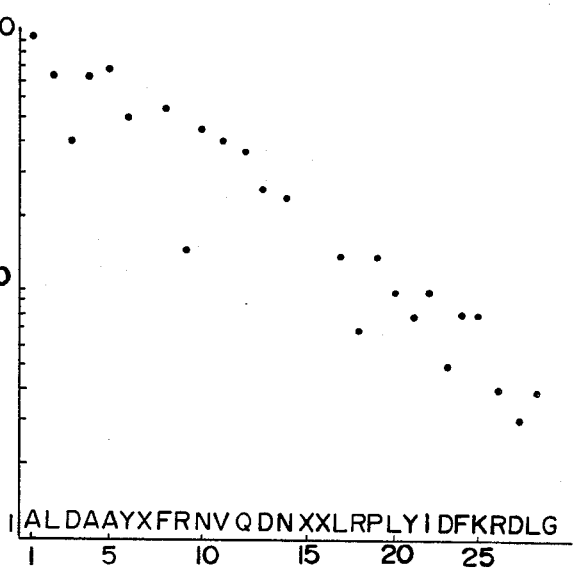
FIG. 3C
Form 3
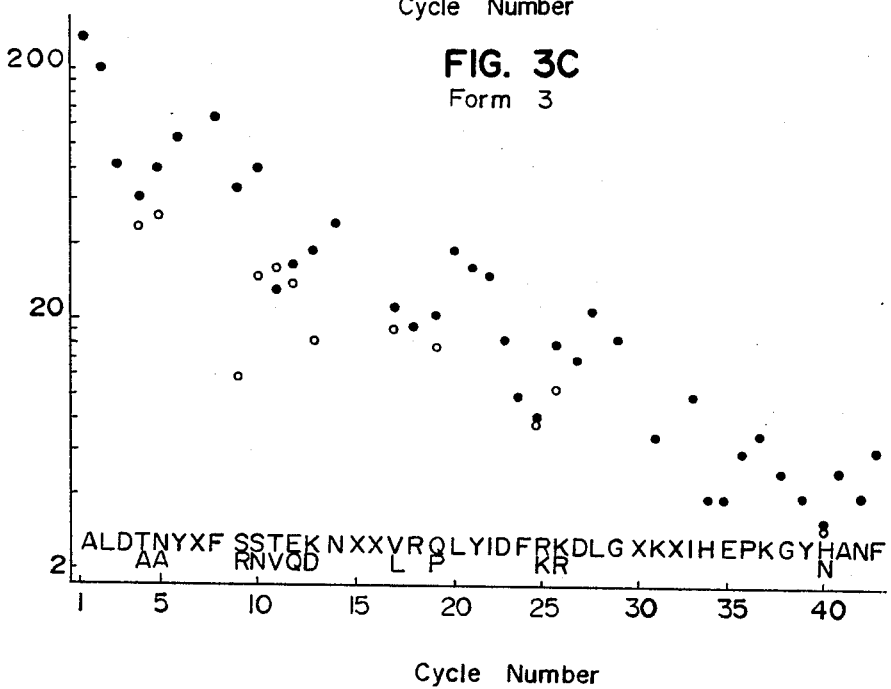
Cycle Number

HETERODIMER FORM OF TRANSFORMING GROWTH FACTOR-BETA

TECHNICAL FIELD

This invention relates to growth factors, and in particular to transforming growth factor-beta (TGF-$\beta$), a multi-functional peptide involved in controlling proliferation, differentiation, and other functions in many cell types.

BACKGROUND ART

Type $\beta$ transforming growth factor (TGF-$\beta$) is a multi-functional, hormonally active polypeptide that is synthesized by many cell types. Virtually all cells have receptors for TGF-$\beta$. See, generally, M. B. Sporn, et al., *Transforming Growth Factor-$\beta$: Biological Function and Chemical Structure*, Science, Vol. 233, p. 532–534 (1986); J. Massague, *The Transforming Growth Factors*, Trends in Biochem. Sci., Vol. 10, p. 239–240 (1985a). Though TGF-$\beta$ was first identified by its ability to cause phenotypic transformation of rat fibroblasts, it is now recognized as having regulatory actions in a wide variety of both normal and neoplastic cells. TGF-$\beta$ influences the rate of proliferation of many cell types, acting as a growth inhibitor and also controlling processes of adipogenesis, myogenesis, chondrogenesis, osteogenesis, epithelial cell differentiation and immune cell function. Increased expression of fibronectin, type I collagen and probably other extracellular matrix components is a widespread early response of cells to TGF-$\beta$. Alterations in the architecture of the extracellular matrix induced by TGF-$\beta$ could be involved in regulating the expression of specific phenotypes by this factor, while certain effects of TGF-$\beta$ on cell proliferation may be secondary to elevated expression of mitogenically active polypeptides.

Recently it has been discovered that TGF-$\beta$ is prototypic of a family of homologous polypeptides that control the development of tissues in organisms from humans to Drosophila. This family includes various inhibins and activins which regulate the ability of cultured pituitary cells to release follicle stimulating hormone, (see, e.g., A. Mason, et al., *Structure of Two Human Ovarian Inhibins*, Biochem. Biophys. Res. Commun., Vol. 135, p. 957–964 (1986)), the Müllerian inhibiting substances (MIS) which inhibits development of the Müllerian duct in mammalian male embryos, (see, R. Cate, et al., *Isolation of the Bovine and Human Genes for Mullerian Inhibiting Substance and Expression of the Human Gene in Animal Cells*, Cell, Vol. 45, p. 685–698 (1986)), and the transcript of the decapentaplegic gene complex which is critical for the development of Drosophila, (see, R. Padgett, et al., *A Transcript From a Drosophila Pattern Gene Predicts a Protein Homologous to the Transforming Growth Factor $\beta$ Family*, Nature, Vol. 325, p. 81–84 (1986). The bioactive domains corresponding to inhibins, activins, MIS and DPP-C transcript share only about 25% to 35% amino acid sequence identity with TGF-$\beta$.

Three structurally distinct cell surface glycoproteins have been identified that specifically bind TGF-$\beta$ with affinity constants in the picomolar range. J. Massague, *The Transforming Growth Factors*, Trends in Biochem. Sci., Vol. 10, p. 239–40 (1985). Since many cell lines display all three types of putative TGF-$\beta$ receptors, it is possible that this family of TGF-$\beta$ receptors might interact with a family of TGF-$\beta$-related polypeptides in a situation similar to that which exists among the receptors for other families of hormonally active agents.

TGF-$\beta$ is highly conserved among mammalian species; mouse and human TGF-$\beta$ differ in amino acid sequence by a single amino acid. To date, TGF-$\beta$, a 25 kDa protein, has been thought to be present in mammals in a single form, a homodimer of two 12.5 kDa chains linked by disulfide bonds. But cf. EPO application 85304848.6, "Polypeptide Cartilage-Inducing Factors Found in Bone" (Inventor: S. Seyedin et al.) (describes two forms of cartilage-inducing factor, CIF-A and CIF-B, each of which is a homodimer, the two forms having different amino acid sequences) with S. Seyedin et al., "Cartilage-inducing Factor-A: Apparent Identity to Transforming Growth Factor-$\beta$," J. of Biol. Chem. Vol. 261, p. 5693–95 (1986).

DISCLOSURE OF INVENTION

The invention relates to a unique form of TGF-$\beta$ which has been found in porcine platelets. The factor, designated TGF-$\beta$3, is a heterodimer having an approximate molecular weight of 25,000 daltons. One strand of the dimer has a partial N-terminal amino acid sequence identical to the partial N-terminal sequence of human platelet TGF-$\beta$ and porcine platelet TGF-$\beta$1, the homodimeric, predominant form of porcine TGF-$\beta$. The other strand of the dimer has a partial N-terminal amino acid sequence identical to TGF-$\beta$2, the homodimeric secondary form of porcine TGF-$\beta$ which has an amino acid sequence quite different from TGF-$\beta$.

BRIEF DESCRIPTION OF DRAWINGS

FIGS. 3a–3c are plots of partial amino acid sequences of TGF-$\beta$ forms 1, 2, and 3, respectively.

BEST MODE FOR CARRYING OUT THE INVENTION

Initial extraction of TGF-$\beta$ from platelets is accomplished by lysing the cells and then centrifuging to remove insoluble material. The supernatant is then precipitated, e.g., with ethanol-ether, resuspended, and fractionated by gel-filtration, such as over a Bio-Gel P-60 column. Further purification may be accomplished by reverse phase HPLC, preferably on successive C-4 and C-18 columns.

Figure 1:
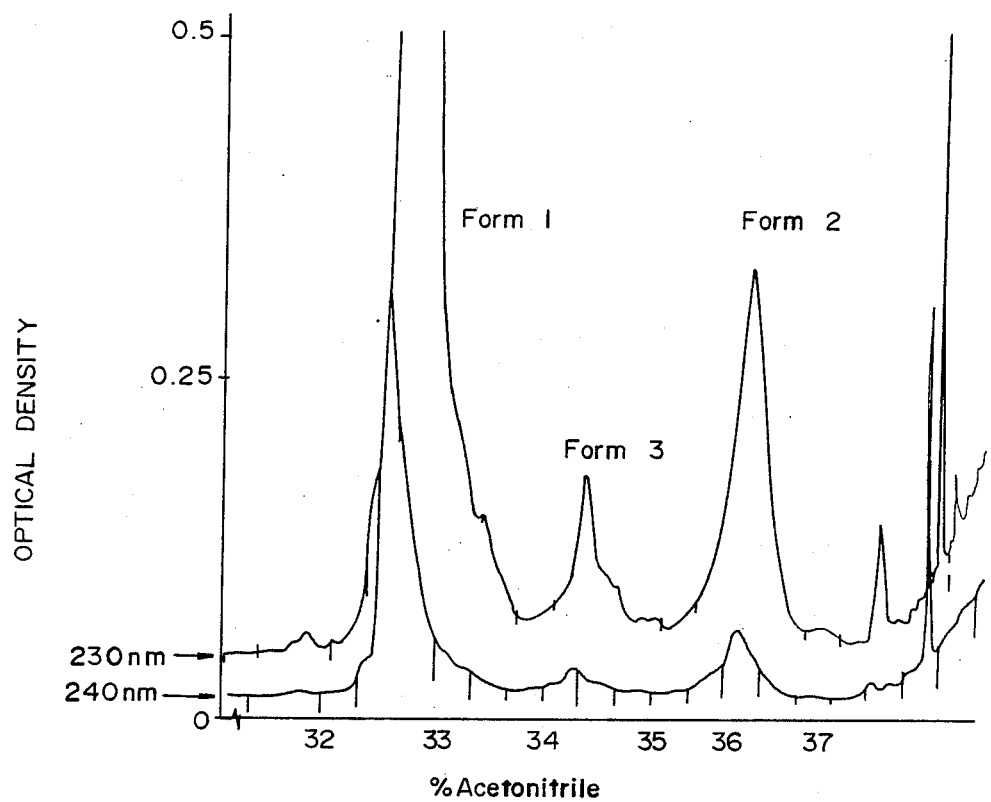
FIG. 1 is an elution curve plotting absorbance at 230 nm and 240 nm against elution of TGF-$\beta$ on a acetonitrile gradient.

Subsequent fractionation on a Synchropak C-4 column resolves the TGF-$\beta$ into three peaks at approximately 32%, 34% and 36% acetonitrile (see FIG. 1). The least hydrophobic peak corresponds to TGF-$\beta$1, a homodimer having an N-terminal amino acid sequence, so far as is known, identical to human TGF-$\beta$. The most hydrophobic peak corresponds to TGF-$\beta$2, a distinct homodimeric form of TGF-$\beta$ having an N-terminal amino acid sequence substantially different from TGF-$\beta$1. The middle peak corresponds to TGF-$\beta$3, a heretofore unreported heterodimer of a single strand each of forms 1 and 2. Each of the forms has an approximate molecular weight of 25 kilodaltons, and has approximately equivalent activity in the TGF-$\beta$ assay, i.e., promotes approximately equivalent growth of unanchored NRK cells in semisolid medium.

Purification of TGF-β from porcine platelets

Fresh porcine blood was obtained from slaughterhouses, and the platelets were extracted by adding a solution of 1% Triton X-100, 0.2M EGTA in a ratio of 1 ml/g, freezing to −20° C. and thawing five times and centrifuging at 5–10×g for 30 minutes to remove insoluble material. Supernatant from the centrifugation was mixed with 4 parts of acidic ethanol, 50 parts of 95% ethanol, 14 parts distilled water, 1 part concentrated HCl and adjusted to pH 5.2 with concentrated ammonium hydroxide, in accordance with the procedure of A. B. Roberts, et al., *Transforming Growth Factors: Isolation of Polypeptides from Virally and Chemically Transformed Cells by Acid/Ethanol Extraction*, Proc. Natl. Acad. Sci. USA, Vol. 77, p. 3494–98 (1980).

The proteins were precipitated with two volumes of cold anhydrous ethanol and four volumes of cold anhydrous ether and allowed to stand for about 20 minutes. Precipitate was collected by centrifugation or rapid filtration through Whatman No. 1 paper and resuspended in 1M acetic acid (about 3–4 ml per gram of tissue). Insoluable matter was removed by centrifugation at about 5–10×g for 10–30 minutes, and the supernatant was then concentrated, as by lyophilization with resuspension in 1M acetic acid.

This suspension was then fractionated over successive Bio-Gel P-60 gel filtration columns (100–200 mesh) in the absence of and then in the presence of urea as described by R. K. Assoian, et al., *Transforming Growth Factor-β in Human Platelets: Identification of a Major Storage Site, Purification and Characterization*, J. Biol. Chem., Vol. 258, p. 7155–7160 (1983). The first elution was done on a 5.0 cm×100 cm column at a flow rate of about 40 ml/h, the column having been equilibrated in 1M acetic acid. 10 ml fractions were collected and those fractions having TGF-β activity (as described below) were pooled and concentrated by lyophilization for further purification.

Active fractions from the first column were dissolved in 5 ml of 1M acetic acid containing 8M ultra-pure urea and gel-filtered on the second Bio-Gel P-60 column (5 cm×80 cm) at a flow rate of about 20 ml/hour, the column equilibrated with the sample solvent. Fractions of 10 ml were collected. (To preclude the formation of cyanate in the solvent, the ultra-pure urea may be dissolved at pH 2 in 1M acetic acid, the resulting solution being adjusted to final conditions by addition of glacial acetic acid and water.) Aliquots of selected column fractions were again tested for TGF-β activity (as described below). Fractions containing the peak of TGF-β activity were pooled and concentrated, e.g., by pressure filtration through an Amicon YM5 membrane.

The pooled TGF-β fractions were further purified at ambient temperature on two successive reverse phase HPLC columns. In the first column, a Synchropak C-4 column (10 mm×250 mm), a linear gradient of 15–30% n-propanol in H$_2$O/0.1% trifluoroacetic acid was used at a flow rate of 1 ml/min, the gradient changing at 0.1%/min. TGF-β eluted at approximately 22% propanol. Fractions having TGF-β activity were pooled and diluted 1:1 with 1M acetic acid to reduce the propanol concentration, and then loaded on the second column, a Synchropak C-18 (10 mm×250 mm). A linear gradient of 20–30% n-propanol in H$_2$O/0.1% trifluoroacetic acid was used on this column at a flow rate of 1 ml/min, the gradient changing at 0.05%/min. TGF-β eluted as a broad peak beginning at approximately 24% n-propanol.

TGF-β from the second HPLC step was again chromatographed over a Synchropak C-4 column (10 mm×250 mm), eluted with a linear gradient of 25–40% acetonitrile in H$_2$O/0.1% trifluoroacetic acid at a flow rate of 1 ml/min, the gradient changing at 0.1%/min. FIG. 1 shows the 230 nm and 240 nm absorbance elution profiles of fractions containing TGF-β. Three distinct protein peaks appear at approximately 32%, 34% and 36% acetonitrile. The least hydrophobic peak is designated TGF-β1, the most hydrophobic TGF-β2, and the middle peak TGF-β3.

Figure 2:
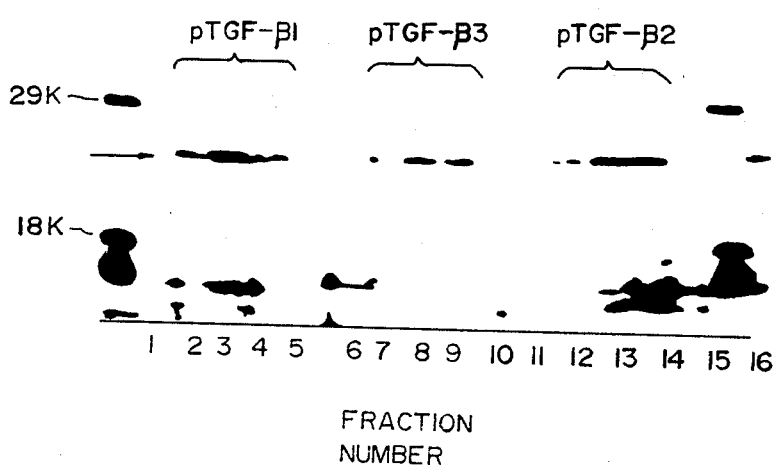
FIG. 2 shows the silver stain from SDS-polyacrylamide gel electrophoresis of TGF-$\beta$ forms 1, 2 and 3.

To confirm the existence of these three distinct peaks, forms 1, 2 and 3 from three different runs were pooled separately. Samples (about 10 ug of protein) from each of these pools were mixed and rechromatographed over the Synchropak C-4 column as described above. Three separate peaks of absorbing material were again produced. Aliquots of fractions across the profile of absorbing material were subjected to SDS-polyacrylamide gel electrophoresis and visualized by silver staining, shown in FIG. 2. The arrow identifies the 25 kDa band present in fractions from all three peaks. Positions of 29 kDa and 18 kDa molecular weight markers are also indicated.

The above procedures yield substantially purified quantities of TGF-β typically in the range of about 2 ug per gram of platelets, representing an approximately 500,000 fold purification. Purity of 95–97% as determined by silver staining of samples run on non-reducing SDS gels, amino acid composition analysis, and N-terminal sequencing is reproducibly achievable.

In quantification of total TGF-β recovered from the above purification, form 1 represented the predominant form (approximately 65–80%) of TGF-β present. The amounts of form 2 and form 3 varied from preparation to preparation with form 3 typically present in a lesser amount (generally about 5–10% of total TGF-β recovered). Quantification may be accomplished by integrating the peaks of the elution curves. Approximate quantification may also be ascertained by cutting out the elution peaks and weighing the cut paper.

Comparison to Human TGF-β

Figure 4A:
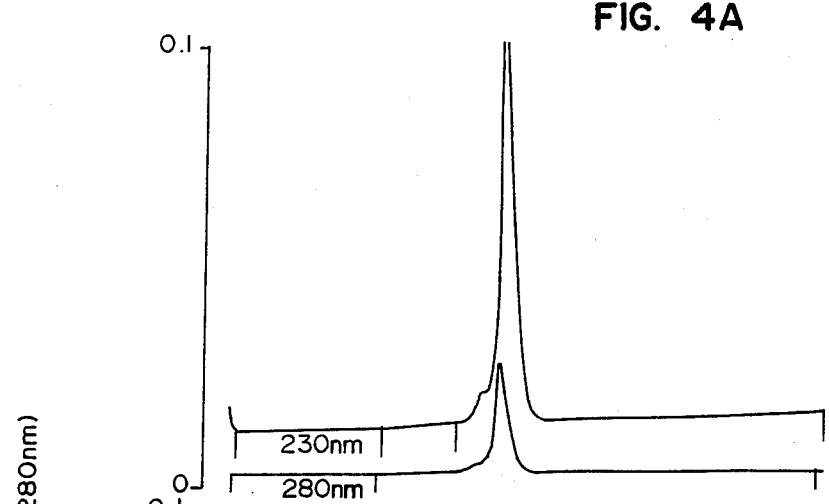
FIGS. 4a–4c are elution curves similar to FIG. 1, comparing human TGF-$\beta$ with porcine TGF-$\beta$1.
Figure 4B:
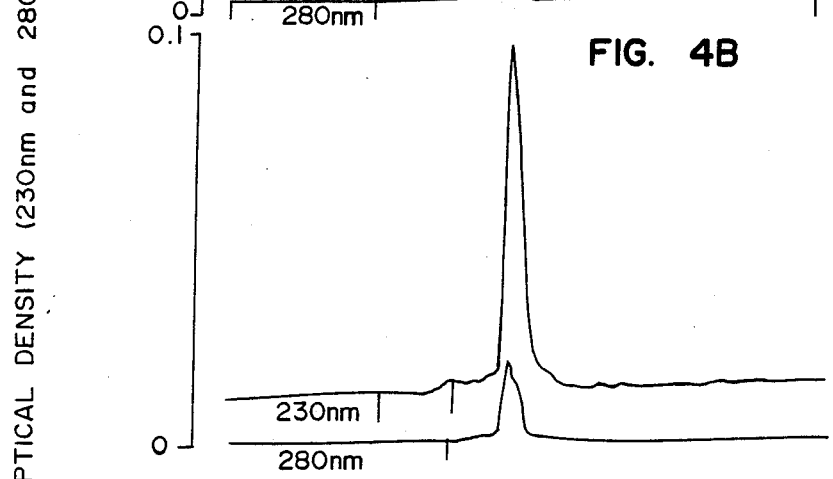
Figure 4C:
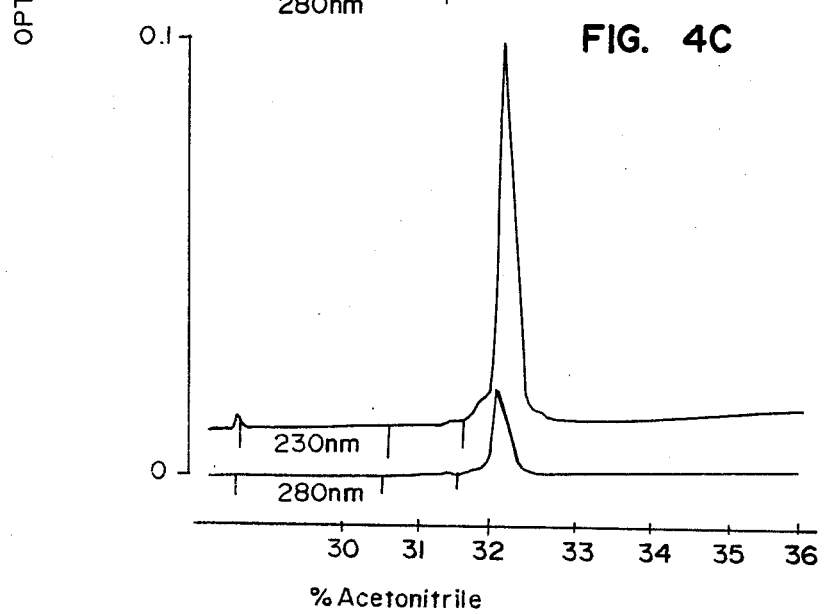

Human platelet TGF-β prepared and analyzed by the above procedures did not yield the three peaks found for porcine TGF-β. FIGS. 4a–4c respectively show elution peaks of 10 ug porcine TGF-β1 (FIG. 4a), 10 ug human TGF-β (FIG. 4b), and a mixture of 5 ug pTGF-β1 and 5 ug hTGF-β (FIG. 4). The single peak of human TGF-β comigrated with porcine TGF-β1, the least hydrophobic of the porcine platelet TGF-β peaks.

TGF-β Activity Assay

Material in each of the three peaks was evaluated in the so-called TGF-β assay to determine activity. This assay determines the ability of the polypeptide to induce anchorage-independent growth in nonneoplastic NRK fibroblasts by measuring the formation of colonies in soft agar.

The test material was sterilized by lyophilization of 1M acetic acid solutions in sterile tubes. The residue was then redissolved in binding buffer at 10 times the final concentration used in the assay and centrifuged to clarity. Samples to be tested were suspended in 0.3% agar (Difco, Noble agar) in Dulbecco's modified Eagle medium (GIBCO) supplemented with 10% calf serum (GIBCO) penicillin (100 units/ml), streptomycin (100 ug/ml) and 5 ng/ml of EGF. A portion (0.7 ml containing 3500 cells of the resultant mixture) was pipetted onto a 0.7 ml base layer (0.5% agar in the supplemented medium) in each of three 35-mm petri dishes. Plates were then incubated at 37° C. for 7 days in a humidified 10% $CO_2$ atmosphere without further feeding.

The assay may be read unfixed and unstained at 1 week. Alternately, the plates may be stained with 0.7 ml of a sterile solution of 2-(p-iodophenyl)-3-(p-nitrophenyl)-5-phenyl tetrazolium chloride (0.5 mg/ml in water) layered over the agar and incubated for 24 hours. After removal of excess dye solution, the plates may be scored in a bright-field microscope (with or without projection onto a screen), counting the number of colonies in a unit field.

TGF-$\beta$ activity is defined as the effective dose (ED) resulting in 50% of maximal colony formation (colony size greater than 3000 um$^2$) in the presence of EGF (2.5 ng/ml). The maximal response of the assay is about 2500 colonies. Each of the three TGF-$\beta$ forms was approximately equivalent in activity in this assay, having an ED$_{50}$ of about 0.1-0.4 ng/ml (ED$_{50}$ being the effective dose yielding 50% of maximal response).

Amino Acid Sequence Analysis of Porcine TGF-$\beta$

Nonreduced samples of 25 kDa TGF-$\beta$1 (180 pmol), TGF-$\beta$2 (130 pmol) and TGF-$\beta$3 (400 pmol) were subjected to N-terminal automated Edman amino acid degradation in the presence of polybrene using an Applied Biosystems Model 470A gas-phase sequenator. Phenylthiohydantoin (PTH) amino acid derivatives were quantitated with a Hewlett-Packard 3390A integrator. Yields are shown in FIGS. 3a-c, corresponding to TGF-$\beta$ forms 1-3, respectively. The amino acid identified in each cycle is indicated. The open symbols in FIG. 3c indicate the yield of PTH amino acid corresponding to the amino acid residue listed in the bottom row of the deduced sequence. FIG. 3 shows only the first 43 residues of TGF-$\beta$3; additional studies have identiied the first 50 residues of the amino acid protein. (Since human TGF-$\beta$ has 112 amino acids and has a molecular weight of 25 kDa, and since pTGF-$\beta$3 is a heterodimer of forms 1 and 2, forms 2 and 3 are believed to also have 112 amino acids.)

The sequence of the N-terminal 50 amino acids of porcine TGF-$\beta$1 was found to be identical to the N-terminal sequence of human TGF-$\beta$, as follows:

```
                    5                      10
    Ala—Leu—Asp—Thr—Asn—Tyr—Cys—Phe—Ser—Ser—Thr—Glu—Lys—Asn—
15                      20                     25
Cys—Cys—Val—Arg—Gln—Leu—Tyr—Ile—Asp—Phe—Arg—Lys—Asp—Leu—
   30                      35                     40
Gly—Trp—Lys—Trp—Ile—His—Glu—Pro—Lys—Gly—Tyr—His—Ala—Asn—
              45                     50
         Phe—Cys—Leu—Gly—Pro—Cys—Pro—Tyr—.
```

In contrast, analysis of TGF-$\beta$2 yielded an N-terminal amino acid sequence that was strikingly different from the sequence of TGF-$\beta$1:

```
                    5                      10
    Ala—Leu—Asp—Ala—Ala—Tyr—Cys—Phe—Arg—Asn—Val—Glu—Asp—Asn—
15                      20                     25
Cys—Cys—Leu—Arg—Pro—Leu—Tyr—Ile—Asp—Phe—Lys—Arg—Asp—Leu—
   30                      35                     40
Gly—Trp—Lys—Trp—Ile—His—Glu—Cys—Cys—Gly—Tyr—Asn—Ala—Asn—
              45                     50
         Phe—Cys—Ala—Gly—Gly—Cys—Pro—Tyr—.
```

N-terminal amino acid sequencing of TGF-$\beta$3 yielded a mixed sequence identical to the combined sequences of TGF-$\beta$1 and TGF-$\beta$2. Those cycles in form 3 corresponding to residues in which TGF-$\beta$1 and TGF-$\beta$2 differed yielded an approximately equimolar amount of both amino acid derivatives. All other cycles yielded a single amino acid derivative corresponding to the residue shared by TGF-$\beta$1 and TGF-$\beta$2 in that position, indicating that TGF-$\beta$3 corresponds to the heterodimer consisting of one chain of TGF-$\beta$1 linked to one chain of TGF-$\beta$2.

At the present time studies have not been completed on the functions of TGF-$\beta$3 in comparison to TGF-$\beta$1 or TGF-$\beta$2. All forms are active in the TGF-$\beta$ assay however, and thus it is apparent that TGF-$\beta$3 possesses at least a portion of the molecular functions of TGF-$\beta$. Consequently it is likely that TGF-$\beta$3 has utilities similar to the contemplated therapeutic utilities of TGF-$\beta$. Such utilities include repair of tissue injury caused by trauma, burns, surgery, or debility in the aged, regulation of metabolic conditions such as osteoporosis, and use as an anti-inflammatory or immunosuppressive agent, among others. See, generally, M. B. Sporn, et al., *Transforming Growth Factor-$\beta$: Biological Function and Chemical Structure*, Science, Vol. 233, p. 532-34 (1986); S. Seyedin, *Cartilage-Inducing Factor-A: Apparent Identity to Transforming Growth Factor-$\beta$*, J. of Biol. Chem., Vol. 261, p. 5693-95 (1986).

What is claimed is:

1. A substantially pure polypeptide growth factor characterized in that the factor is found in mammalian platelets, has activity in the TGF-$\beta$ assay, and is a heterodimeer having an apparent molecular weight of 25,000 daltons as determined by SDS-PAGE, one of the chains of the dimer having the N-terminal amino acid sequence:

$$
\begin{array}{c}
\phantom{Ala-Leu-Asp-Ala-}\overset{5}{\phantom{Ala}}\phantom{-Tyr-Cys-}\overset{10}{\phantom{Phe}}\\
\text{Ala—Leu—Asp—Ala—Ala—Tyr—Cys—Phe—Arg—Asn—}\\
\overset{15}{\phantom{XX}}\phantom{XXXXXXXX}\overset{20}{\phantom{XX}}\\
\text{—Val—Glu—Asp—Asn—Cys—Cys—Leu—Arg—Pro—Leu—}\\
\overset{25}{\phantom{XX}}\phantom{XXXXXXXX}\overset{30}{\phantom{XX}}\\
\text{—Tyr—Ile—Asp—Phe—Lys—Arg—Asp—Leu—Gly—Trp—}\\
\overset{35}{\phantom{XX}}\phantom{XXXXXXXX}\overset{40}{\phantom{XX}}\\
\text{—Lys—Trp—Ile—His—Glu—Cys—Cys—Gly—Tyr—Asn—}\\
\overset{45}{\phantom{XX}}\phantom{XXXXXXXX}\overset{50}{\phantom{XX}}\\
\text{—Ala—Asn—Phe—Cys—Ala—Gly—Gly—Cys—Pro—Tyr—}
\end{array}
$$

and the other chain of the dimer having the N-terminal amino acid sequence:

$$
\begin{array}{c}
\overset{5}{\phantom{XX}}\phantom{XXXXXXXX}\overset{10}{\phantom{XX}}\\
\text{Ala—Leu—Asp—Thr—Asn—Tyr—Cys—Phe—Ser—Ser—}\\
\overset{15}{\phantom{XX}}\phantom{XXXXXXXX}\overset{20}{\phantom{XX}}\\
\text{—Thr—Glu—Lys—Asn—Cys—Cys—Val—Arg—Gln—Leu—}\\
\overset{25}{\phantom{XX}}\phantom{XXXXXXXX}\overset{30}{\phantom{XX}}\\
\text{—Tyr—Ile—Asp—Phe—Arg—Lys—Asp—Leu—Gly—Trp—}\\
\overset{35}{\phantom{XX}}\phantom{XXXXXXXX}\overset{40}{\phantom{XX}}\\
\text{—Lys—Trp—Ile—His—Glu—Pro—Lys—Gly—Tyr—His—}\\
\overset{45}{\phantom{XX}}\phantom{XXXXXXXX}\overset{50}{\phantom{XX}}\\
\text{—Ala—Asn—Phe—Cys—Leu—Gly—Pro—Cys—Pro—Tyr—.}
\end{array}
$$

2. The factor of claim 1 wherein the platelets are porcine platelets.

* * * * *